United States Patent [19]
Hutter, Jr. et al.

[11] 3,964,106
[45] June 22, 1976

[54] THREE-PART TOTAL KNEE PROSTHESIS

[75] Inventors: Charles G. Hutter, Jr.; Luigi Gentile, both of North Hollywood, Calif.

[73] Assignee: Physical Systems, Inc., North Hollywood, Calif.

[22] Filed: Mar. 3, 1975

[21] Appl. No.: 554,484

[52] U.S. Cl. .............................. 3/1.911; 128/92 C
[51] Int. Cl.² ........................................ A61F 1/24
[58] Field of Search ...................... 3/1, 1.9–1.911; 128/92 C

[56] References Cited
UNITED STATES PATENTS

| | | | |
|---|---|---|---|
| 3,765,033 | 10/1973 | Goldberg et al. | 3/1.911 |
| 3,816,855 | 6/1974 | Saleh | 128/92 C X |
| 3,869,731 | 3/1975 | Waugh et al. | 128/92 C X |

OTHER PUBLICATIONS

"The Total Walldius Knee Endoprosthesis in Combination with Retropatellar Facet Replacement (Polyethylene), Indication, Operative Procedure, and, Clinical Results in a Two-year Follow-up Study", by H. F. Von Andrian–Werburg et al., *Journal of Biomedical Materials Research Symposium,* No. 5 (Part 2), pp. 289–298, 1974, presented at Clemson University, Apr. 14–18, 1973.

*Primary Examiner*—Ronald L. Frinks
*Attorney, Agent, or Firm*—Fulwider Patton Rieber Lee & Utecht

[57] ABSTRACT

A prosthesis that replaces the articulating surfaces of the knee joint with mechanical devices which are designed to reproduce its function. A portion of the lower end of the femur is removed and replaced by a cap while the upper tibia is cut off and replaced by a tibial plateau. The articulating surface of the patella is modified to permit fixation of a third component which articulates with a groove in the anterior part of the femoral cap.

5 Claims, 15 Drawing Figures

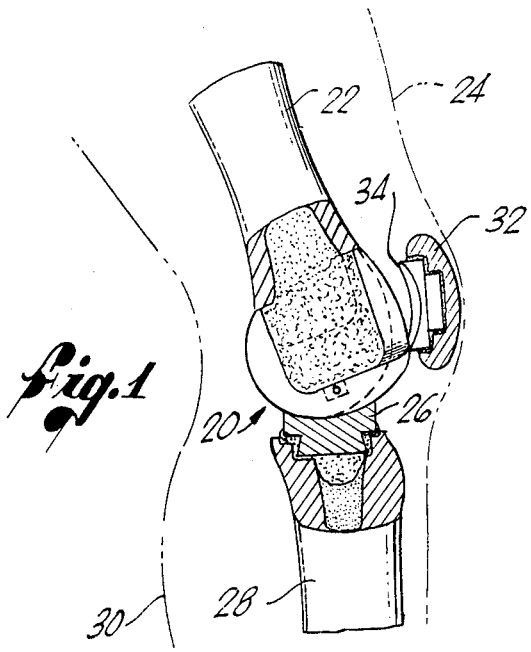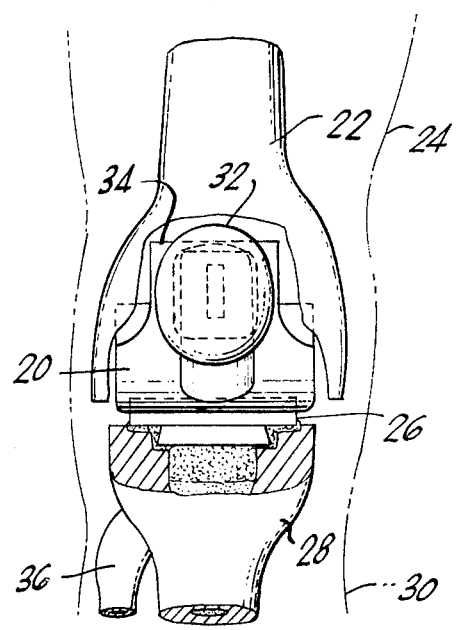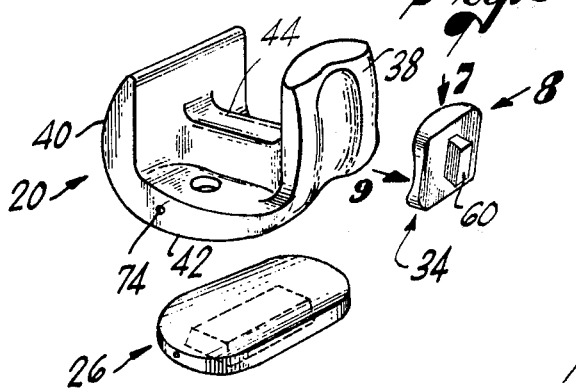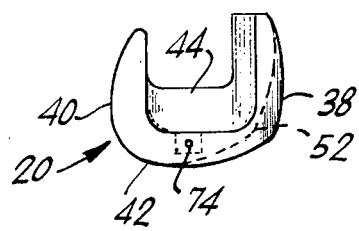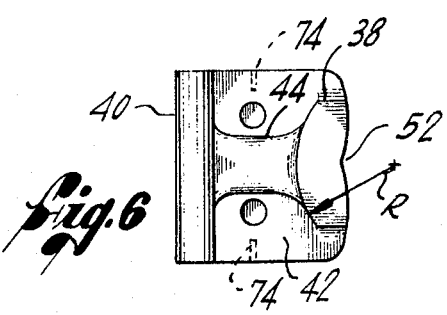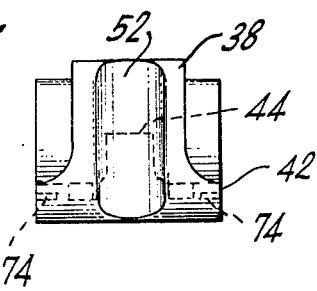

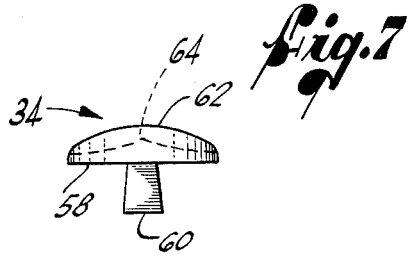
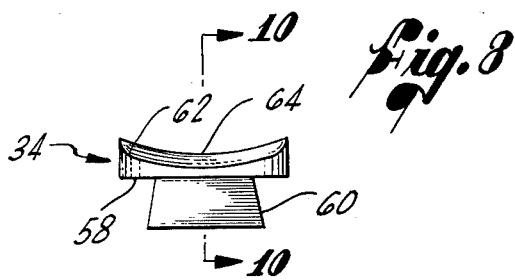
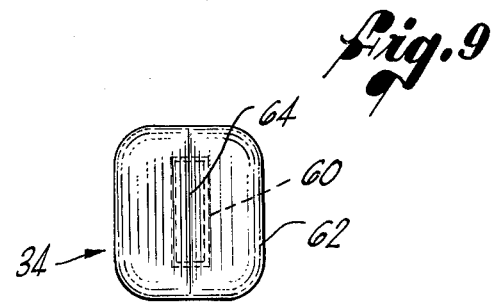
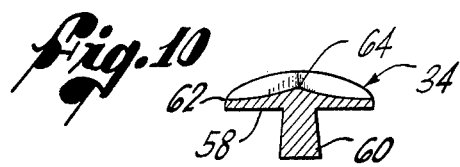
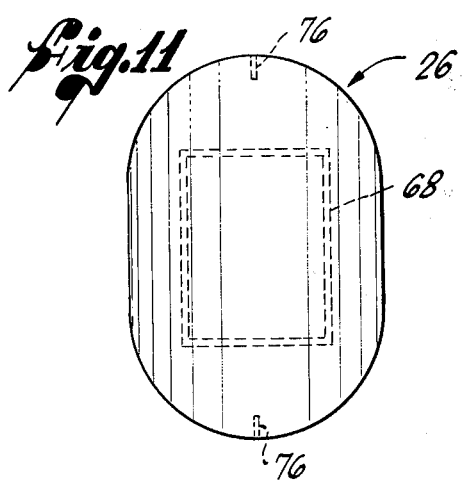
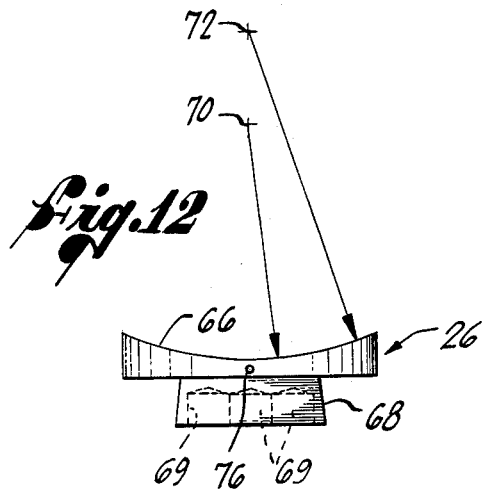
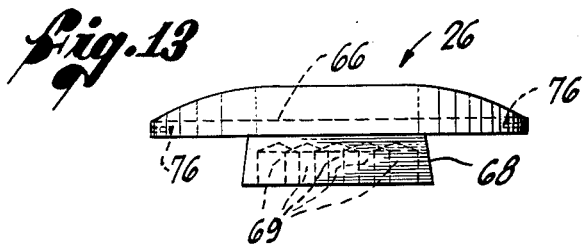

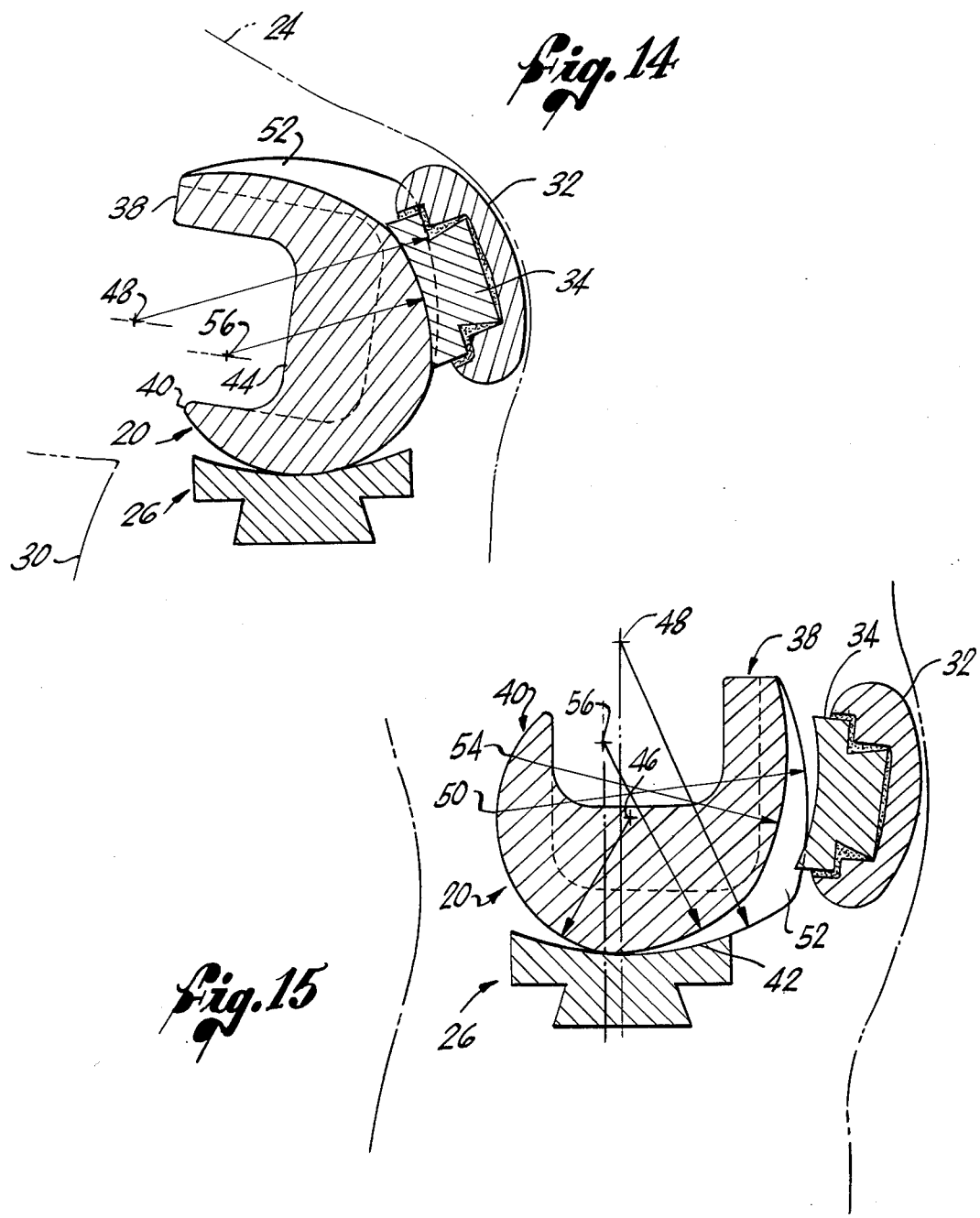

THREE-PART TOTAL KNEE PROSTHESIS

BACKGROUND OF THE INVENTION

A number of different knee prostheses have been developed; these falling into two general types, the first type being of the hinged variety, wherein a shaft such as a metal nail or spike, is driven into each of the bones and the two shafts are then hingedly connected together, as by axle means of one form or another. The second form of prosthesis involves cutting away of the mating surfaces of the femur and tibia and replacing these surfaces by members having specially designed mating surfaces, wherein one of the members slides across the other, more or less in the manner that the femur slides on the tibia in a normal knee joint. While this form of prosthesis operation has been performed before, this was the usual extent of the operation, and although results were generally satisfactory, a number of problems remained. It has now been found that if a new articulating surface is placed on the posterior aspect of the patella, much better results are obtained. The present invention makes use of an improved design for the femoral and tibial bearing surfaces, as well as making provision for a patellar articulating metal implant. Their design provides for knee joint stability as well as low friction articulation.

The need for the knee prosthesis strikes across the entire population. Arthritis of the knee, from injury or disease, is common and the pain, instability and stiffness which may result is totally disabling to the afflicted individual. Treatment by stiffening the knee is unacceptable, as the person is not then able to arise from a chair or step up a curb. Only prosthetic replacement of the knee joint avoids this disability and only the three-part joint offers the opportunity to walk up the stairs and climb slopes without pain.

SUMMARY OF THE INVENTION

In the present invention, a portion of the condylar surfaces of the femur is removed and a suitable cap is cemented onto the distal or lower end of the femur. The opposing articulating surfaces of the tibia are then removed and are replaced by a plateau which is cemented to the upper end of the tibia. The patella, or knee cap, has its posterior or articulating rear surface shaped to receive a patellar component, shaped to engage in a groove in the femoral cap. The femoral cap and the tibial plateau are so shaped that they cooperate to provide a limit stop when the knee is in the extended position and a low friction joint when the knee is flexed. Their shape also prevents antero-posterior displacement of these bones.

The patella component provides a low friction, painless gliding surface for the powerful quadriceps tendon which is so important to extension of the knee. This patellar component acts as a pulley mechanism in the notch in the femoral cap.

DESCRIPTION OF FIGURES

FIG. 1 is a side elevational (lateral) view of a complete knee joint, partially in section, with the outline of the knee indicated in phantom outline;

FIG. 2 is a front elevational view of the right knee showing the elements of the prosthesis in their proper position;

FIG. 3 is an exploded perspective showing the three elements of the prosthesis as they appear separated from the knee;

FIG. 4 is a side elevational view of the femoral cap;

FIG. 5 is a front elevational view of the femoral cap;

FIG. 6 is a top plan view of the femoral cap;

FIG. 7 is a top plan view of the patellar block taken in the direction of the arrow 7 in FIG. 3;

FIG. 8 is a side elevational view of the patellar block taken in the direction of the arrow 8 in FIG. 3;

FIG. 9 is a posterior view of the patellar block taken in the direction of the arrow 9 FIG. 3;

FIG. 10 is a cross-sectional view of the patellar block taken on the line 10—10 of FIG. 8;

FIG. 11 is a top plan view of the tibial plateau;

FIG. 12 is an end elevational view of the tibial plateau;

FIG. 13 is a front elevational view of the plateau;

FIG. 14 is a lateral view of the knee joint, similar to FIG. 1, with the knee in flexed position; and FIG. 15 is a lateral view, similar to FIG. 14, with the leg extended and "locked."

Referring now to the drawings, and particularly to FIG. 1 thereof, the numeral 20 indicates generally a femoral cap that is cemented to the lower end of the femur 22 that is located in the thigh 24 of a person. The lower end of the femoral cap 20 rests upon and bears against a tibial plateau 26 that is cemented to the the upper end of the tibia 28 of the lower leg 30. The kneecap or patella 32 has a block 34 mounted in its rear side and this block bears against and rides over the femoral cap 20. It will be recognized that this is a showing of the right knee and the view is of the lateral or outside of the knee. FIG. 2 is a view of the right knee from the front, and may be defined as an anterior view. In FIG. 2, the same elements are shown including the femoral cap 20, the femur 22, the thigh 24, the tibial plateau 26, the tibia 28 and the lower leg 30. In addition, the kneecap or patella 32 is shown and the patellar block 34 is indicated. There is also shown the fibula bone 36 that is found adjacent the tibia 28.

In FIG. 3, an exploded perspective view is shown of the various elements, including the femoral cap 20, the tibial plateau 26 and the patellar block 34. FIGS. 4, 5 and 6 show the femoral cap in somewhat greater detail, with additional details being indicated in FIGS. 14 and 15. The cap 20 is preferably made of a suitable plastic, such as an ultrahigh molecular weight polyethylene, and the tibial plateau 26 and the patellar block 34 are made of a suitable metal, such as 316 stainless steel, titanium, or cobalt chrome stainless steel. Clearly, all materials must be inert and not react with body fluids, etc. It is to be understood that the elements of the prosthesis are not restricted to the materials mentioned, since other materials can be used. All such materials are intended to be included in the term "compatible bearing material" as used herein. If materials of differing hardness are used, the patellar block 34 should be of the harder material. The femoral cap 20 can then be of softer material, and the tibular plateau 26 should be of the harder material.

The femoral cap 20, shown in FIGS. 4, 5 and 6, is a generally U-shaped block having anterior and posterior sections 38 and 40, respectively, connected by a distal section 42. The anterior section 38 is higher than the posterior section 40, as shown in FIG. 4, but the posterior section is wider than the anterior, as shown in FIG. 6. Extending between the anterior and posterior sections is a web 44 approximately half the height of the anterior section, the web having approximately the same thickness as its height. This relationship is clearly indicated in FIG. 5.

The exterior surface of the posterior section 40 is formed as an arc whose center of curvature 46 is indicated in FIG. 15. This point 46 is the center of rotation about which the tibula rotates, and as indicated particularly in FIG. 15, the arc extends from the upper portion of the posterior section 40 to a point on the distal section 42 that is substantially in line with the center line of the femur 22. The remainder of the surface of the distal section 42 is formed as an arc whose center of curvature 48 is located above and slightly rearwardly of the point 46. The major portion of the outer surface of the anterior section 38 is formed as an arc whose center of curvature is located at the point 50 on the rear surface of the anterior section 40.

As seen in FIGS. 4, 5 and 6, the anterior and distal sections 38 and 42 of the femoral cap 20 have a central groove 52 in which the patellar block 34 rides. In the anterior section 38 the base of the groove 52 follows a curve whose center is located at 54, and this curve blends into another curve along the distal section 42, the center of the distal section curvature being located at point 56, all as shown in FIG. 15.

One of the purposes of the patella is to position and guide the patellar ligament across the knee, as the leg is flexed. Since this ligament is so importantly involved in the straightening or extending of the leg, it is important that the patella be retained in the same position as in a normal functioning knee, and the groove 52 is intended to accomplish this. The patella block 34, in addition to being shown in FIG. 3, is shown in FIGS. 7 through 10, where it is seen that the block 34 is a relatively flat member, generally rectangular, having a flat anterior surface 58 intended to be set into the patella 32 and held therein by a protrusion or boss 60 with diverging sides so that the cross-section of the boss is smallest adjacent the anterior surface 58 and largest at its other or free end. In this way, as hereinafter described, the patella block 34 can be securely held in the patella 32 with a generally wedging action that prevents the loosening or removal of the block from the patella.

The posterior surface 62 of the patella block 34 is curved in a vertical plane, as seen in FIG. 8, so that the block 34 corresponds essentially to the curvature of the anterior surface of the femoral cap 20. In addition to the curvature of the posterior surface 62 in a vertical plane, the surface is also curved in a horizontal plane as best seen in FIGS. 7 and 10.

As indicated in those figures, the posterior surface 62 of the patellar block 34 has a compound curved shape, being convex in a horizontal plane, concave in a vertical plane, and is then additionally given a cusped shape in the center, as best seen in FIG. 10. The ridge of peak 64 of the cusp fits into the groove 52 of the femoral cap 20, and the patellar block 34 is thus held against transverse movement, while being free to move longitudinally with respect to the femoral cap.

The patella is moved across the femur each time the leg is flexed, and in some elderly persons the patella has been worn quite thin. This means that the patellar block 34 must be sufficiently strong to carry the load imposed on the patella 32, and the block must extend only a slight distance into the patella so that the latter is not greatly weakened.

As previously mentioned, the patellar block 34 is formed of a hard material that will not react with body fluids or tissues, and the tibial plateau 26 is formed of a similar material. The tibial plateau is the plate or bearing member upon which the femoral cap rests, and since the plateau bears the full weight of the body, if not more, it must be of rugged construction and solidly anchored. To this end, it is formed of a fairly heavy plate of metal whose upper or proximal surface is curved from front to rear (anterior to posterior) to provide a concave surface 66, as shown in FIG. 12, into which the femoral cap 20 fits. The medial and lateral ends of the plateau 26 are rounded, as shown in FIG. 11, and as a result, an anterior or posterior view of the plateau has the appearance indicated in FIG. 13. As in the case of the patellar block 34, the opposite surface of the plateau 26 is provided with a boss 68 having flaring sides, so that, as hereinafter described, the plateau may be held in the tibia with a wedging action.

To provide additional surface for the cement used to anchor the tibial plateau in place, there is provided a series of recesses or holes 69 extending inwardly into the boss 68 from the distal surface of the boss.

The central portion of the surface 66 has a curve of somewhat smaller radius whose center is indicated by the point 70 in FIG. 12, while the anterior and posterior portions of the curve have a somewhat longer radius whose center is indicated by the numeral 72. These curves, together with the corresponding curves of the femoral cap 20, provide a locking action that limits the forward or anterior movement of the tibia 28 with respect to the femur 22. The posterior movement of the tibia is not similarly limited, and consequently, the person experiences very normal movement and control of the leg.

While it is apparent that the various elements of the total knee prosthesis may be made in various sizes to fit individual requirements, it has been found that elements constructed in accordance with the following dimensions are quite satisfactory.

| Femoral cap 20 | | |
|---|---|---|
| Width —medial to lateral side | 63.5 | mm. |
| Anterior to posterior surface | 56.8 | mm. |
| Height | 51.6 | mm. |
| Width of anterior member | 34.5 | mm. |
| Width of web 44 | 16. | mm. |
| Height of Web 44 | 15.2 | mm. |
| Distance from point 46 to posterior surface 50 | 25.4 | mm. |
| Distance from point 48 to distal surface 42 | 52.2 | mm. |
| Distance from point 50 to anterior surface | 57.2 | mm. |
| Distance from point 54 to anterior base of groove 52 | 50.8 | mm. |
| Distance from point 56 to distal base of groove 52 | 38.1 | mm. |
| Patellar block 34 | | |
| Height | 25.4 | mm. |
| Width | 25.4 | mm. |
| Maximum thickness of block | 6.35 | mm. |
| Radius of central portion of surface 62 in vertical plane | 38.1 | mm. |
| Radius of curves in horizontal plane forming cusp 64 | 48.1 | mm. |
| Tibial plateau | | |
| Anterior-posterior maximum distance | 43.2 | mm. |
| Medial-lateral maximum | 63.5 | mm. |
| Radius of curvature central portion (point 70 to surface 66) | 38.1 | mm. |
| Radius of curvature of outer portions of surface 66 (point 72 to surface) | 50.8 | mm. |

It will be appreciated that these dimensions are by way of example only and are primarily to give an appreciation of the magnitude and proportion of the various pieces.

In reconstructing a knee in accordance with the present invention, the knee joint is first exposed and the patella with attached ligaments is laid to one side. The lower or distal end of the femur is then cut to provide a flat surface that is approximately 11 mm. above or proximally from the original lowermost surface of the femur. This surface is substantially perpendicular to the longitudinal axis of the femur being only very slightly displaced from the perpendicular because of the angulation of the femur. The center of the distal end is notched to receive the web 44, and the anterior surface of the femur 22 is cut so that the cortex thereof bears against the upper edge of the anterior section 38 and the posterior surface is cut so that it bears against the posterior section 40. Methyl methacrylate or other quick setting cement is applied to the cut surface of the femur and to the interior surfaces of the femoral cap 20 so that the cap is firmly attached to the femur 22.

To insure the proper alignment of the femoral cap 20 and the tibial plateau 26, the cap 20 is provided with holes 74 at each end, these holes being centered and aligned with the axis of the cap, and being adapted for engagement by an alignment tool. Similar holes 76 correspondingly located in the tibial plateau 26 are engaged by a similar alignment tool so that the cap and plateau can be properly aligned with each other, the femur and the tibia. By way of example only, the alignment tools may take the form of a pliers-like tool having opposing pins on the ends of the jaws.

It should be noted that the load on the femur is transmitted to the femoral cap 20 by means of the cortex of the femur which is an intrinsically strong material. Previous prosthetic devices that have relied upon means that extend into the interior of the femur and transmit the load through that portion have frequently failed in use, since the interior of the bone is relatively soft and weak and any load applied to that material breaks down the material and causes the attached member to be driven up into the femur.

The upper or proximal end of the tibia is trimmed approximately 3 mm., the minimum thickness of the tibial plateau, and a space is cut into the tibia to receive the boss 68. The cut end of the bone is coated with cement, as is the corresponding surface of the tibial plateau 26, and the plateau is then inserted into the upper end of the tibia.

One of the advantages of this prosthesis is that it is possible to improve the operation of the knee. Thus, if the ligaments that hold the knee together have become loose or stretched, it is possible to locate the bearing suraces of the femoral cap and the tibial plateau so that the femur and the tibia are separated slightly further from each other, thereby tightening the ligaments. On the other hand, if desirable, more of the end of the femur and of the tibia may be cut away so that the two bones are closer to each other and the ligaments are loosened.

The patellar block 34 is inserted in the patella 32 by cutting a slideway in the posterior surface of the patella, so that the block may be slid into the patella to assume the position in FIGS. 14 and 15. Of course, a quick-setting cement such as methyl methacrylate cement is used to hold the block in the proper position in the patella.

The femur, tibia and patella are then returned to their proper positions and the incision is closed. Normally, recovery will be rapid and, depending upon the previous condition of the knee, the result will be a satisfactorily functioning knee joint.

While there has been shown a preferred form of the invention, it is to be understood that modifications may be made therein and consequently, the invention is not to be restricted to the particular form, arrangement of parts, or dimensions herein described and shown, except as limited by the following claims.

We claim:
1. A knee prosthesis which includes:
   a femoral cap having a proximal surface adapted to bear against the cortex of the femur to transmit the load carried by the femur to the cap, and a distal surface having a plurality of curvatures, said cap having a vertical groove in its anterior surface;
   a tibial plateau having a distal surface adapted to bear against the cortex of the tibia, with a boss extending away from said femur and toward said tibia for attachment to the latter, and having a proximal surface adapted to cooperate with the distal surface of said femoral cap, said proximal surface of said plateau having a central curved surface having a radius of curvature less than that of the adjacent proximal surface, said curvature of said femoral cap and said tibial plateau being coordinated so that the tibia rotates about a constant center when flexing, and the difference between said central and adjacent radii of curvature of said tibial plateau effects a limiting stop when said tibia is extended; and
   a patellar block adapted to be mounted on the posterior of the patella, the posterior surface of said block being curved to cooperate with the adjacent surface of said femoral cap, and having a vertically extending cusp fitting into said vertical groove of said femoral cap.

2. A knee prosthesis as described in claim 1 in which said femoral cap is formed of a high strength inert plastic and said tibial plateau and said patellar block are formed of a hard inert metal, whereby contacting members are of different materials.

3. A knee prosthesis as described in claim 1 in which said patellar block has a boss on its anterior surface extending toward said patella.

4. A knee prosthesis as described in claim 1 in which said cusp of said patellar block engages said groove of said femoral cap to prevent transverse movement of said patellar block, while permitting longitudinal movement thereof.

5. A knee prosthesis as described in claim 2 in which said patellar block has a boss on its anterior surface extending toward said patella, and said cusp of said patellar block engages said groove of said femoral cap so that said block is free to move longitudinally in said groove, but is held against transverse movement.

* * * * *